United States Patent [19]
Ridinger et al.

[11] Patent Number: 5,556,380
[45] Date of Patent: Sep. 17, 1996

[54] METHOD FOR REMOVING FIBRIN SHEATHS FROM CATHETERS

[75] Inventors: Mark T. Ridinger; Paul V. Suhocki, both of Durham, N.C.

[73] Assignee: Duke University, Durham, N.C.

[21] Appl. No.: 417,018

[22] Filed: Apr. 5, 1995

[51] Int. Cl.$^6$ .......................... A61B 17/36; A61M 25/01
[52] U.S. Cl. ..................... 604/52; 604/267; 606/113
[58] Field of Search ..................... 604/267, 164, 604/264, 52; 606/200, 106, 110, 113, 114, 127, 159

[56] References Cited

U.S. PATENT DOCUMENTS

| | | |
|---|---|---|
| 798,839 | 9/1905 | Stowe. |
| 1,772,352 | 8/1930 | Huber. |
| 3,791,387 | 2/1974 | Itoh. |
| 4,568,338 | 2/1986 | Todd. |
| 4,694,838 | 9/1987 | Wijayarthna. |
| 4,738,667 | 4/1988 | Galloway. |
| 4,927,426 | 5/1990 | Dretler. |
| 5,071,649 | 12/1991 | Hunter. |
| 5,098,441 | 3/1992 | Wechler. |
| 5,108,420 | 4/1992 | Marks. |
| 5,171,233 | 12/1992 | Amplatz et al.. |
| 5,192,286 | 3/1993 | Phan et al.. |
| 5,274,768 | 12/1993 | Traw et al. ........................ 395/275 |
| 5,290,229 | 3/1994 | Paskar. |
| 5,330,482 | 7/1994 | Gibbs et al.. |
| 5,341,815 | 8/1994 | Cofone et al.. |
| 5,342,371 | 8/1994 | Welter et al. ........................ 606/113 |
| 5,387,219 | 2/1995 | Rappa ........................ 606/113 X |

OTHER PUBLICATIONS

The Retriever—Endovascular Snare by Target Therapeutics, Aug. 27, 1992.

*Primary Examiner*—Randall L. Green
*Assistant Examiner*—A. T. Nguyen
*Attorney, Agent, or Firm*—Nixon & Vanderhye P.C.

[57] ABSTRACT

A medical device especially adapted to remove biological material (e.g., fibrin sheath) from the distal end of a patient-internal catheter includes a tubular element, a central wire positioned within the tubular element and a snare wire attached at one end to the central wire so as to form an acute angle therewith, and at its other end to the tubular member. The snare wire includes a proximally extending segment which follows a course of about 360° about the distal end of the tubular member, and thus may be positioned adjacent the catheter's distal end. By effecting relative rotation between the central wire and the tubular member (for example, by rotating the central wire about its longitudinal axis while maintaining the tubular member stationary) will cause the snare wire segment to wrap around the catheter's distal end. Thereafter, manipulation of the device so as to advance the wrapped snare wire segment in a distal direction will strip the biological material from the distal end of the catheter.

4 Claims, 2 Drawing Sheets

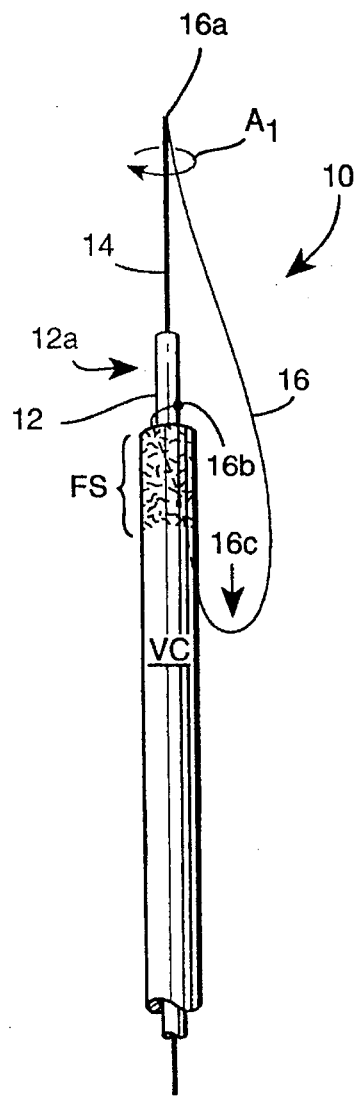
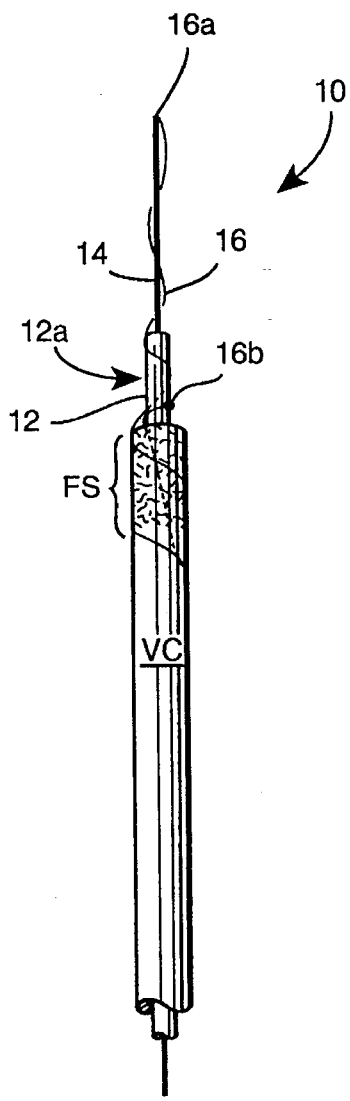
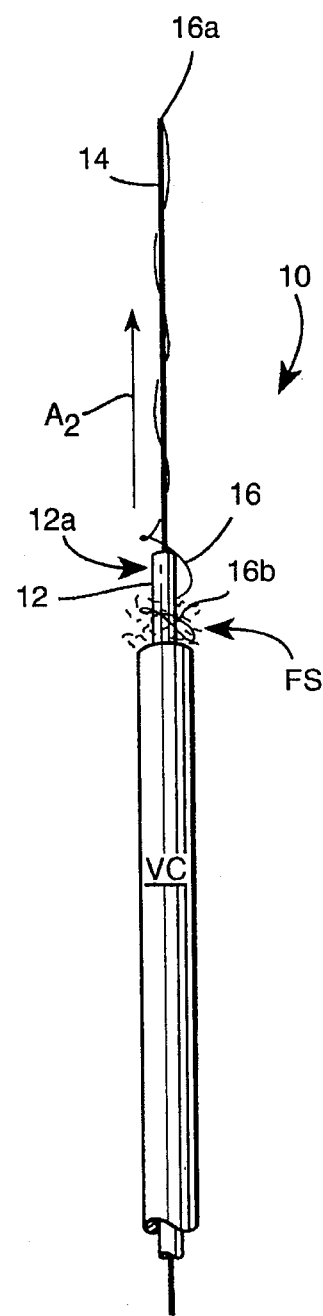
FIG. 2A  FIG. 2B  FIG. 2C

METHOD FOR REMOVING FIBRIN SHEATHS FROM CATHETERS

RELATED APPLICATIONS

This application may be deemed to be related to U.S. patent application Ser. No. 08/417,019 filed even date herewith in the name of the same inventors as the present application, the entire content of which is expressly incorporated hereinto by reference.

FIELD OF INVENTION

The present invention relates generally to the field of medical devices. More particularly, the present invention relates to the field of snares used during medical procedures to remove material from a patient. In its preferred embodiments, the present invention is especially adapted to remove fibrin sheaths from the distal ends of intravascular catheters.

BACKGROUND AND SUMMARY OF THE INVENTION

Catheters formed of a biocompatible plastics material are sometimes implanted in patients to relieve various symptoms and/or to assist in medical procedures. For example, central venous catheters have been implanted into a patient's vein during vascular surgery. One problem associated with such implanted catheters, however, is that a fibrin sheath (which is a deposit of fibrin and platelets) may form on the implanted catheter, initially at the entrance site into the vein and then along the length of the catheter. While it usually takes weeks to months for the fibrin sheath to form, it has been reported to form in as little as 24–48 hours following implant.

The fibrin sheath can cause catheter dysfunction, usually being manifested by the physician being able to infuse through, but not to aspirate from, the catheter. Intraluminal urokinase may then be administered several times to exclude the possibility of intraluminal clotting. If intraluminal urokinase treatment is ineffective, fluoroscopy may then be performed to allow the physician to evaluate catheter tip location and to obtain evidence of fibrin sheath formation.

Once the presence and extent of the fibrin sheath have been identified, the physician must take the necessary steps to remove the sheath from the implanted catheter. While it is conceivable that the implanted catheter may be removed and replaced surgically, it is more desirable for the fibrin sheath to be removed without surgical removal of the implanted catheter.

Presently, there are basically two approaches which may be employed without removal of the implanted catheter. The first approach involves introducing percutaneously a gooseneck snare (e.g., a snare device generally disclosed in U.S. Pat. No. 5,171,233 to Amplatz et al, the entire content of which is incorporated expressly hereinto by reference) into the patient's groin area. The snare is then advanced through the patient's femoral vein to the catheter implant site, at which time it is manipulated so that the snare encircles the distal end of the implanted catheter so that the fibrin sheath may be stripped therefrom. While the fibrin sheath which is stripped from the distal end of the implanted catheter travels to the patient's lung, surgical removal has been shown to result in embolization as well.

Another technique that has been employed to strip fibrin sheaths from the distal ends of implanted catheters is to introduce a J-tipped wire intraluminally through the implanted catheter. Rotation of the J-tipped wire about the distal end of the implanted catheter will thus strip a portion of the fibrin sheath therefrom. While this technique is advantageous since the implanted catheter serves as a guide passageway (i.e., separate incisions to access the femoral vein are unnecessary), the J-tipped wire is typically only capable of removing less than all of the fibrin sheath from the implanted catheter due to its size limitations.

What has been needed in this art, therefore, is a medical device which is capable of being guided intraluminally through an implanted catheter, but which is capable of removing substantially all of the fibrin sheath that may have formed at the catheter's distal end. It is towards fulfilling such a need that the present invention is directed.

Broadly, the present invention is embodied in medical devices having a snare loop for removing patient-internal biological material from an implanted catheter (e.g., a fibrin sheath which may form at the distal end of a venous catheter) which may be inserted intraluminally through the catheter during a medical procedure. The tubular member has a length sufficient to allow its distal end portion extend beyond the distal end of the patient-internal catheter. A central wire element is movably positioned within the elongate tubular member and has a sufficient length so that its terminal end potion extends distally beyond said distal end of said tubular member.

Importantly, a snare wire is provided such that one of its ends is attached to the central wire with the other end attached to the distal end of said tubular member after completing approximately 360° wrap around the tubular member between the ends. The snare wire, between its attached ends, will include a segment which extends proximally at an acute angle and may therefore be located upon manipulation of the device adjacent the distal end of the patient-internal catheter. Relative rotation between the central wire and the tubular member (e.g., by rotating the central wire about its longitudinal axis while maintaining the tubular member stationary or vice versa) causes said snare wire segment to be wrapped around said distal end of the patient-internal catheter. Distal advancement of this wrapped snare wire segment relative to said distal end of the patient-internal catheter will therefore strip the biological material therefrom.

Further aspects and advantages of this invention will become more clear after careful consideration is given to the following detailed description of the preferred exemplary embodiment thereof.

BRIEF DESCRIPTION OF THE DRAWINGS

Reference will hereinafter be made to the accompanying drawings wherein like reference numerals throughout the various FIGURES denote like structural elements, and wherein;

FIGS. 2A–2C are schematic elevational views showing a sequence of the device depicted in FIG. 1 during use.

DETAILED DESCRIPTION OF THE PREFERRED EXEMPLARY EMBODIMENTS

Figure 1:
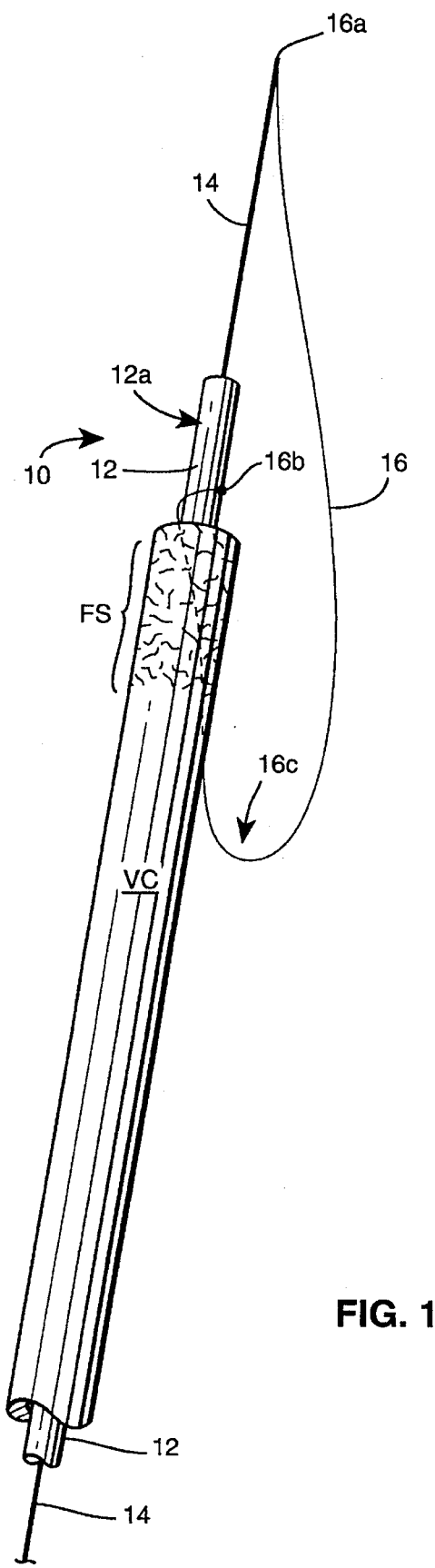
FIG. 1 is a schematic perspective view of a preferred medical snare device embodying the present invention.

One preferred embodiment of a medical snare device 10 according to the present invention is shown in accompanying FIG. 1. The snare device 10 is depicted schematically as being positioned intraluminally within a venous catheter VC, it being understood that the distal end region of venous catheter VC will in use be implanted within a patient's vein. The distal end section of the venous catheter VC is depicted in accompanying FIG. 1 as having a fibrin sheath FS extending proximally along the catheter's exterior surface.

The snare device 10 is generally comprised of an elongate tubular member 12 and a central wire element 14 which is movably positioned within the lumen of the tubular member 12. Each of the tubular member 12 and central wire element 14 is of sufficient length to allow the physician to intraluminally insert them as a unit through the venous catheter VC so that the distal end 12a of the tubular body 12 is capable of extending distally beyond the distal end of the venous catheter VC, and so that the terminal end 14a of the central wire element 14 is capable of being extended beyond the distal end 12a of the tubular member (e.g., to achieve relative positioning as shown in FIG. 1).

Important to the present invention, the snare device 10 includes a snare wire 16 formed of a flexible metal or plastics wire, thread or the like. The snare wire 16 has its distal end 16a physically attached to the central wire element 14 so as to form an acute angle therewith and its proximal end 16b physically attached (e.g., via biocompatible epoxy, heat-welding, imbedding or the like) to the tubular member 12 at or near its distal end 12a. The ends 16a, 16b are thus axially separated from one another along the length of the device 10 so as to form a snare loop collectively with the terminal end 12a of the tubular member and that length of the central wire element 14 extending therebeyond. As shown, the snare wire 16, between the ends 16a and 16b is preferably wrapped approximately 360° around the tubular member 12 so that the end 16b faces distally.

The relative diameters of the central wire 14 and the snare wire 16 are dependent in large part upon the particular medical procedure in which the device 10 of this invention is intended to be employed. It is preferred, however, that the diameters of the central wire 14 and the snare wire 16 each be within the range of about 0.001 to about 0.040 inch. Moreover, it is preferred that the snare wire 16 have a lesser diameter as compared to the central wire element 16 so that the former is relatively more flexible, while the latter is relatively more stiff. Therefore, it is preferred that the ratio of the central wire diameter to the snare wire diameter be between about 1.1:1 to about 10.0:1.

The snare wire 16 is of sufficient length between its ends 16a, 16b such that a segment 16c thereof may be positioned proximally of the end 16b adjacent the distal end of the venous catheter. With the snare wire segment 16c positioned in such a manner, the physician may rotate the central wire element 14 about its longitudinal axis within the lumen of the tubular member 12 as shown by arrow $A_1$ in FIG. 2A. Relative rotation between the central wire element 14 and the tubular member 12 (e.g., rotation of the central wire element 14 while maintaining the tubular member 12 stationary) will thereby cause the snare wire segment 16c to be wrapped or twisted more or less helically about the exterior surface of the venous catheter's distal end as shown in FIG. 2B. The several turns of the wrapped snare wire segment 16c will thus be brought into contact with the fibrin sheath FS at the distal end of the venous catheter VC. As such, advancement of the central wire 14 and/or the tubular member 12 in a distal direction (arrow $A_2$ in FIG. 2C) will, in turn, cause the wrapped snare wire segment 16c to be moved distally along the exterior surface of the distal end of the venous catheter VC thereby stripping the fibrin sheath FS therefrom.

Although the central wire element 14 has been depicted in the accompanying drawing FIGURES as including an eyelet 14a at its terminal end, it will be appreciated that the eyelet 14a is not critically necessary since the end 16a of the snare wire 16 may be bonded to the central wire's terminal end via biocompatible epoxy, solder, or the like. Furthermore, the central wire 14 and the snare wire 16 may be formed as a single (unitary) monofilament wire, instead of the separate, but connected, wires as shown in the accompanying drawing FIGURES.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A procedure for removing a fibrin sheath from a distal end of a venous catheter comprising:

(i) intraluminally advancing a medical device having a tubular member, a central wire positioned within said tubular member and a snare wire connected at one end to said central wire and at another end to said tubular member;

(ii) manipulating said medical device to position a segment of said snare wire proximally of said another end thereof adjacent the fibrin sheath at the distal end of the venous catheter;

(iii) effecting relative rotation between said central wire and said tubular member to cause said snare wire segment to wrap around the distal end of the venous catheter; and then (iv) causing said wrapped snare wire segment to advance in a distal direction relative to the distal end of the venous catheter to thereby strip the fibrin sheath therefrom.

2. The procedure as in claim 1, wherein step (iii) is practiced by rotating said central wire about its longitudinal axis while maintaining said tubular member stationary.

3. The procedure as in claim 1, wherein step (iv) is practiced by advancing at least one of said central wire and said tubular member in a distal direction.

4. The procedure as in claim 1, wherein step (iv) is practiced by advancing said central wire in a distal direction while maintaining said tubular member stationary.

* * * * *